United States Patent
Choi et al.

(10) Patent No.: US 10,613,022 B2
(45) Date of Patent: Apr. 7, 2020

(54) METHOD FOR FOCUSING LIGHT TO TARGET OBJECT WITHIN SCATTERING MEDIUM

(71) Applicant: Korea University Research and Business Foundation, Seoul (KR)

(72) Inventors: Wonshik Choi, Seoul (KR); Seungwon Jeong, Seoul (KR); Ye-Ryoung Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 11 days.

(21) Appl. No.: 16/137,670

(22) Filed: Sep. 21, 2018

(65) Prior Publication Data

US 2019/0277748 A1   Sep. 12, 2019

(30) Foreign Application Priority Data

Mar. 7, 2018   (KR) .................. 10-2018-0026881

(51) Int. Cl.
*G01N 21/17*   (2006.01)

(52) U.S. Cl.
CPC ....... *G01N 21/17* (2013.01); *G01N 2201/064* (2013.01)

(58) Field of Classification Search
CPC ........ A61B 5/00; A61B 5/0059; G01N 21/17; G01N 2201/064
See application file for complete search history.

(56) References Cited

U.S. PATENT DOCUMENTS

| 8,721,077 B2 | 5/2014 | Vermeer et al. |
| 2014/0023255 A1* | 1/2014 | Lim .............. G06T 11/005 382/131 |
| 2014/0036272 A1 | 2/2014 | Nadkarni |
| 2016/0061725 A1* | 3/2016 | Choi .............. G01N 21/4795 356/497 |
| 2019/0212761 A1* | 7/2019 | Swanson ........ G01J 3/4406 |

FOREIGN PATENT DOCUMENTS

| JP | 6181013 B2 | 8/2017 |
| KR | 10-1688873 B1 | 12/2016 |

OTHER PUBLICATIONS

Choi et al. "Measurement of the Time-Resolved Reflection Matrix for Enhancing Light Energy Delivery into a Scattering Medium", PRL 111, 243901, (2013) (Year: 2013).*

* cited by examiner

*Primary Examiner* — Hina F Ayub

(74) *Attorney, Agent, or Firm* — NSIP Law

(57) ABSTRACT

Disclosed is a method for focusing light to a target object within scattering medium comprising the following steps: (a) illuminating a plurality of incidence beams having different incidence patterns from each other, and obtaining reflection beams which are reflected from the target object for each incidence beams by a flight time which is a arrival time of the reflection beam to a camera; (b) forming a time-gated reflection matrix using the plurality of the incidence beams and the plurality of the reflection beams; (c) applying the time-gated reflection matrix to Single Value Decomposition such that a time-gated eigenchannel corresponding to a depth of the target object is calculated; (d) illuminating an eigen incidence beam having an incidence pattern, to which the time-gated eigenchannel is applied, to the target object.

4 Claims, 18 Drawing Sheets

(7 of 18 Drawing Sheet(s) Filed in Color)

METHOD FOR FOCUSING LIGHT TO TARGET OBJECT WITHIN SCATTERING MEDIUM

CROSS REFERENCE TO RELATED APPLICATION(S)

This application claims the benefit under 35 USC 119(a) of Korean Patent Application No. 10-2018-0026881 filed on Mar. 7, 2018 in the Korean Intellectual Property Office, the entire disclosure of which is incorporated herein by reference for all purposes.

TECHNICAL FIELD

The present invention relates to a method for focusing light to the target object within scattering medium. More specifically, the present invention relates to a method for focusing light to the target object within scattering medium, the method being capable of effectively focusing light to the target object embedded deeply within scattering medium.

BACKGROUND ART

Target objects are often embedded within disordered environments in many important in vivo applications such as bio-medical imaging, phototherapy, and optogenetics. In these applications, it is necessary to deliver light waves to a deeply embedded target object for efficient optical imaging, sensing, and light stimulation.

However, a random wave diffusion induced by multiple light scattering on the disordered environments drastically limits the ability to reach the target object. When waves are propagating inside scattering medium, the waves are spread in both space and time, and only a small fraction of the injected energy reaches the target object.

A simple solution for increasing an arrival distance would be to increase the injecting energy, but this solution will increase a background noise and induce unwanted damage to the sample. Thus, to extend a working depth of optical methodologies, it is necessary to develop a method that increase the efficiency of energy delivery to the embedded target object.

In the past decades, numerous studies demonstrated the control of light waves traversing a scattering medium. The underlying concept of the past decades is to control the wavefront of illumination light to tailor an interference of multiple-scattered waves. In a work by Vellekoop et al. "Focusing coherent light through opaque strongly scattering media (Opt Lett 32, 2309-2311, doi:Doi 10.1364/Ol.32.002309, 2007), it is verified that a light wave transmitted through a scattering layer was focused by the wavefront shaping of an incident wave. Afterwards, temporal as well as spatial focusing has been realized by using broadband light sources.

Meanwhile, adaptive optics is one of the most representative approaches concerning the wave control within a scattering medium. The adaptive optics corrects sample-induced phase retardations and single-scattered waves by using a wavefront shaping device. However, the adaptive optics can control only a tiny fraction of the internal waves for the deeply embedded target object because the single-scattered waves are orders of magnitude weaker than the multiple-scattered waves.

Time-reversal of the ultrasonically modulated light waves is another approach that enables focusing optical waves to the acoustic focus within the medium. However, the concept was demonstrated using the transmitted wave through scattering medium, but it need to use phase-conjugation of the backscattered waves to warrant its utility for in vivo applications.

Also, a feedback control of the wavefront to increase a fluorescence signal from fluorophores embedded within a scattering layer is another approach to enhance light energy delivery to the target object, but this requires labeling agents. In addition, the operation is not target specific since all the fluorophores within the sample are affected.

DISCLOSURE

Technical Problem

Accordingly, the present invention has been made keeping in mind the above problems occurring in the related art, and an object of the present invention is to provide a method for focusing light to the target object within scattering medium being capable of effectively focusing light to the target object embedded deeply within scattering medium.

Technical Solution

In order to accomplish the above objects, the present invention provides a method for focusing light to a target object within scattering medium comprising the following steps: (a) illuminating a plurality of incidence beams having different incidence patterns from each other, and obtaining reflection beams which are reflected from the target object for each incidence beams by a flight time which is a arrival time of the reflection beam to a camera; (b) forming a time-gated reflection matrix using the plurality of the incidence beams and the plurality of the reflection beams; (c) applying the time-gated reflection matrix to Single Value Decomposition such that a time-gated eigenchannel corresponding to a depth of the target object is calculated; (d) illuminating an eigen incidence beam having an incidence pattern, to which the time-gated eigenchannel is applied, to the target object.

Herein, the Single Value Decomposition in step (c) is processed by formula $$R = U\Lambda V^\dagger$$

wherein R is the time-gated reflection matrix, V is an unitary matrix whose columns contain eigenchannels at a incidence plane of the incidence beam, U is an unitary matrix whose columns contain eigenchannels at a reflection plane of the reflection beam, and $\Lambda$ is a diagonal matrix having singular values as diagonal elements; and the time-gated eigenchannel is calculated by using eigenchannels at the columns of the matrix V.

Further, the columns of the matrix V are converted to a two-dimensional complex amplitude image in the incidence plane such that the eigen incidence beam is formed in the step (d).

Further, the time of the time-gated reflection matrix is calculated for a flight time of the incidence beam to the depth of the target object in scattering medium.

Advantageous Effects

According to above-described configuration of the present invention, the present invention can provide a method for focusing light to a target object within scattering medium being capable of effectively focusing light to the target object embedded deeply within scattering medium.

DESCRIPTION OF DRAWINGS

The patent or application file contains a least one drawing executed in color. Copies of this patent or patent application publication with color drawing(s) will be provided by the Office upon request and payment of the necessary fee.

MODE FOR INVENTION

Hereinbelow, various embodiments of the present invention will be described in detail with reference to the accompanying drawings.

Figure 1:
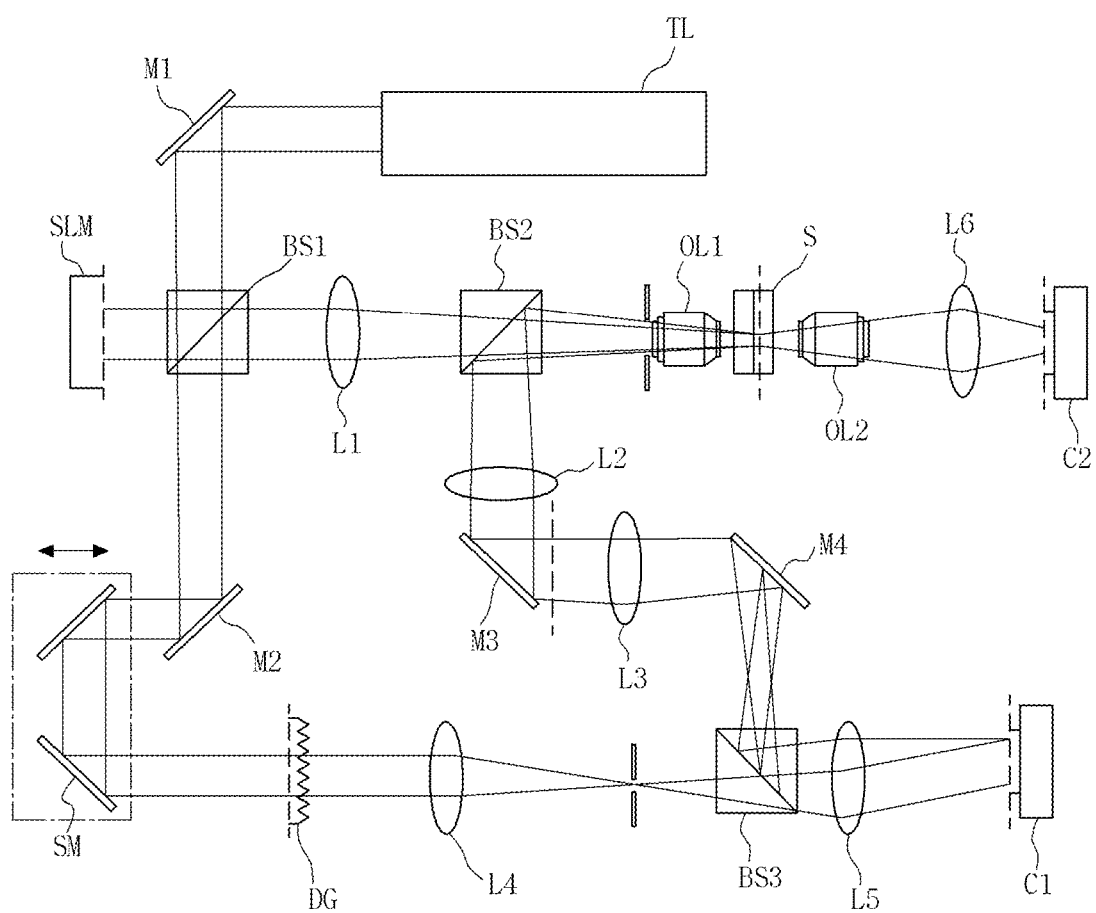
FIG. 1 is an experimental setup for calculating a time-gated eigenchannel in a method for focusing light to a target object within scattering medium according to the present invention.

FIG. 1 is an experimental setup for calculating a time-gated eigenchannel in a method for focusing light to a target object within scattering medium according to the present invention. Referring to FIG. 1, an interference microspore system is applied as one example. The interference microspore system uses a Ti-Sapphire femtosecond laser TL with a center wavelength of 780 nm and a pulse width of 52 fs and Mach-Zhender interferometer.

The light from the laser TL is divided into a sample beam and a reference beam at a beam splitter BS1. A spatial light modulator (SLM) is disposed in the path of the sample beam, and adjusts an incidence pattern of light, that is an incidence angle of light incident to a sample. The sample beam passing through the spatial light modulator goes through beam splitters BS1 and BS2, and is incident into the sample passing through an object lens OL1. And then, the sample beam which reflected from the target object after passing through the scattering medium goes to a camera C1 after passing through the beam splitters BS2 and BS3. Herein, the sample beam reflected from the sample through the beam splitter BS3 meats the reference beam and then an interference image is generated by interference between the sample beam and the reference beam, thereby the interference image is obtained by the camera.

In the above configuration, a diffraction grid DG is arranged at the light path of the reference beam, and the reference beam which is diffracted at the diffraction grid DG is filtered out, then the filtered reference beam generates an off-axis hologram with the reflection beam reflected from the sample. Also, a scan mirror SM is arranged at the light path of the reference beam, and can control the length of the light path of the reference beam, such that the length of the light pat of the reference beam corresponding to the depth of the target object can be controlled and a time-gated reflection matrix described later can be obtained.

Also, in the present invention, transmission intensity of the incidence beam is measured by measuring light transmitted through the sample by using an extra camera C2 for verifying an efficiency of light energy delivery of a time-gated reflection eigenchannel which is described later. The light transmitted through the sample passes through an objective lens OL2 and is captured by the camera C2.

Herein, beam splitters BS3, BS4, BS5 and lenses L2, L3, L4, L5, L6, L7, L8, L9, L10, L11, L12 are arranged at the light path of the sample beam, the reflection beam and the reference beam.

Reference numbers M1, M2, M3, and M4 in FIG. 1 which are not explained are mirrors for changing the path of the sample beam and the reference beam, and reference numbers L1, L2, L3, L4, L5, and L6 are lenses which is arranged at the path of the light. Herein, the setup in FIG. 1 is one example, thus the arrangement for constructing Mach-Zhender interferometer could be changed.

Figure 2:
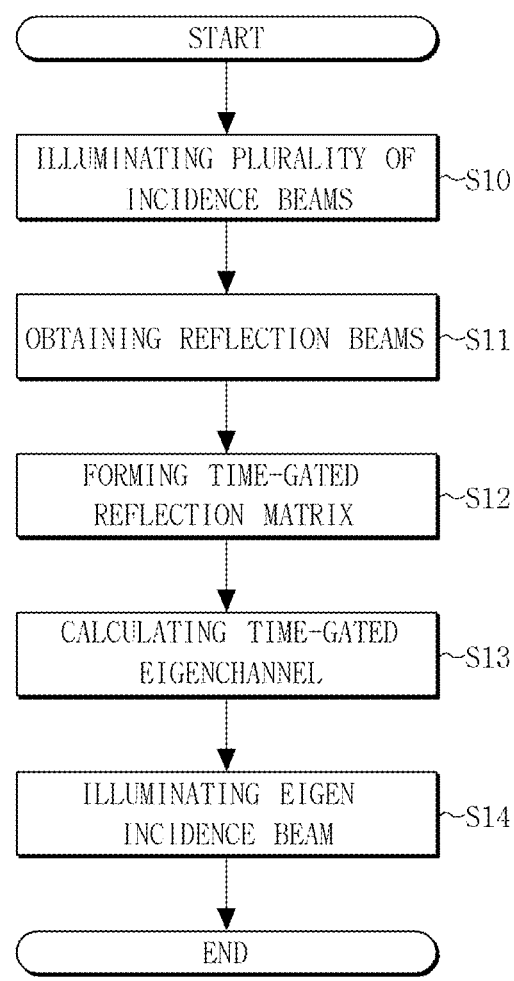
FIG. 2 explains a method for focusing light to a target object within scattering medium according to the present invention.

FIG. 2 explains a method for focusing light to a target object within scattering medium according to the present invention, and uses the experimental setup as shown in FIG. 1 as one example.

Firstly, a plurality of incidence beams having different incidence patterns from each other, for example, n-times of the incidence beams sequentially illuminates the sample S10. The different incidence patterns are generated by changing the incidence angle of the incidence beam. Herein, the sample comprise the scattering medium and the target object deeply within the scattering medium. In the present invention, n times, e.g. 1,600 times of the incidence beam having the incidence pattern which is composed of the plurality of the incidence angle illuminate by using the spatial light modulator, as explained above.

And then, reflection beams which are reflected from the target object in the sample for each incidence beams are obtained by the camera S11, 1,600 of the interference images can be obtained, as mentioned above. Herein, the reflection beams which are reflected from the target object are obtained by a flight time which is a arrival time of the reflection beam to the camera.

Figure 3A:
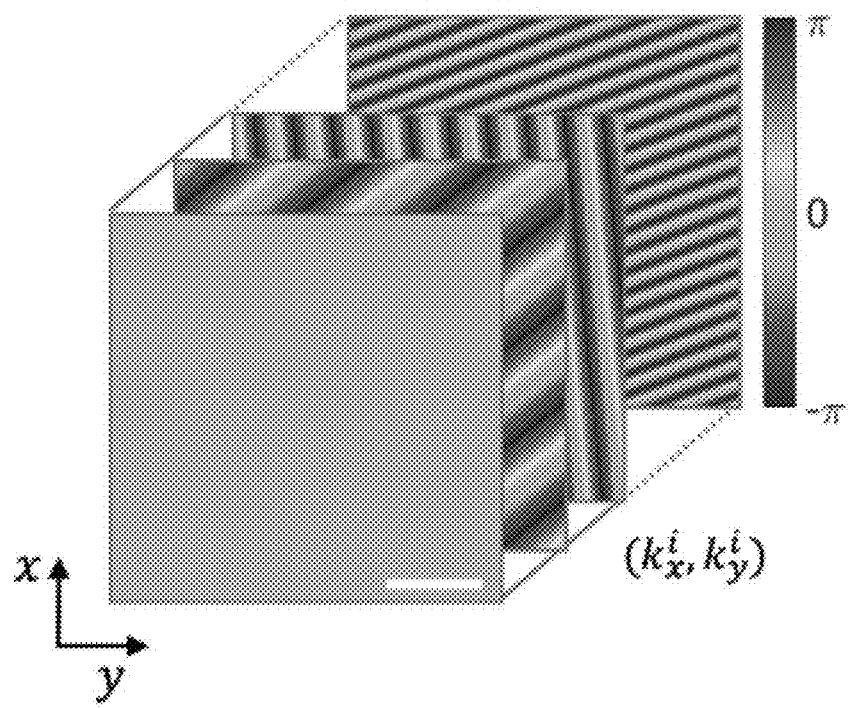
FIGS. 3a to 3c show an incidence beam, an reflected beam, and a time-gated reflection matrix, respectively, in a method for focusing light to a target object within scattering medium according to the present invention.

FIG. 3a show the incidence beams which has the different incidence patterns from each other. Herein, when a difference of path length between the sample beam and the reference beam is within the coherence distance, an interference pattern is generated, and a complex image of the reflection beam can be obtained by selecting an interference component through a Fourier transform of the interference component.

As mentioned above, when the complex images for the plurality of the reflection beams are obtained, a time-gated reflection matrix is formed by using the incidence beams and the reflection beams S12. Herein, the time-gated reflection matrix is calculated for a flight time of the incidence beam to the target object.

Figure 3B:
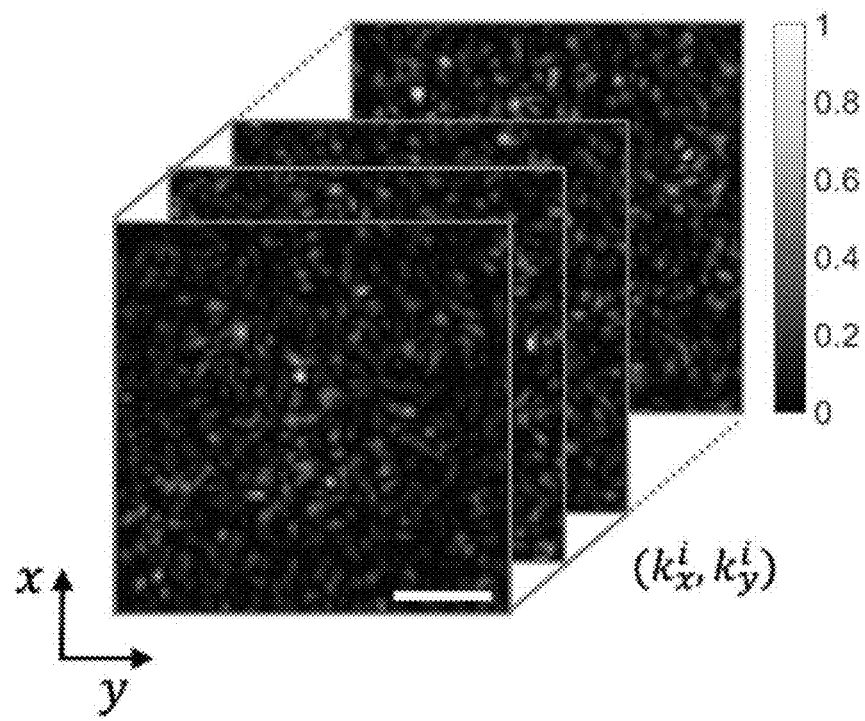

In more detail, in the experimental setup in FIG. 1, a transverse wavevector of the incidence wave $\vec{k}^i = (k_x^i, k_y^i)$ of the incidence beam is scanned by writing linear phase ramps of various orientations and slopes on the spatial light modulator. Herein, the angular scanning range spans up to the numerical aperture of 0.4, and the number of incidence wavevectors are 1,600, as mentioned above, to cover the orthogonal free modes for the view field of 40×40 $\mu m^{2\mu m^2}$ FIG. 3b shows an example of the representative amplitude maps of the backscattered waves $E_0(\vec{r}_0; \vec{k}^i, \tau_0)$, acquired for each $\vec{k}^i$. Herein, the objective focus is set to the depth of the target object so that $\vec{r}_0 = (x, y)$ corresponds to the spatial coordinates at the target plane where the target object is placed. As shown in FIG. 3a, complex field maps $E_0(\vec{r}_0;$ $\vec{k}^i, \tau_0$) of the phase ramps written on the spatial light modulator is used as an input basis. Also, $\vec{r}_i$=(x,y) is the same as $\vec{r}_0$ because the focus of illumination is matched to that of the collection.

The time-gated reflection matrix according to the present invention is described as $R(\vec{r}_0; \vec{r}_i, \tau_0)$, elements of the time-gated reflection matrix consist of the complex amplitude at a detection point $\vec{r}_0$ and a specific flight time $\tau_0$ for the illumination of a unit-amplitude incidence wave at a position $\vec{r}_i$. For this purpose, the set of measured images in FIG. 3b that is the amplitude map is reshaped to form a reflection matrix $M_0(\vec{r}_0; \vec{k}_i, \tau_0)$ by converting individual images into columns of the reflection matrix.

Figure 3C:
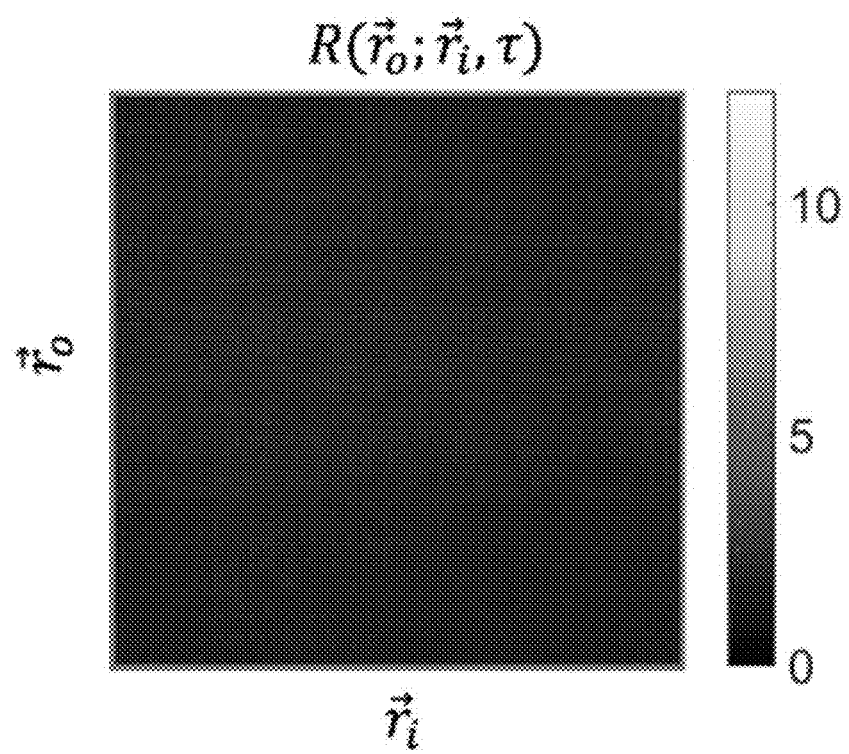

Similarly, an incidence matrix $M_i(\vec{r}_i; \vec{k}_i, \tau_0)$ is constructed from the input basis in FIG. 3a. And then the time-gated reflection matrix is calculated by the matrix multiplication of the incidence matrix and the reflection matrix $R(\vec{r}_0; \vec{r}_i, \tau_0) = M_0(\vec{r}_0; \vec{k}_i, \tau_0) M_0(\vec{r}_0; \vec{k}_i, \tau_0)^{-1}$, thus the time-gated reflection matrix which is described as amplitude map as shown in FIG. 3C can be calculated.

As mentioned above, when the time-gated reflection matrix is calculated, a time-gated eigenchannel is calculated S13 by using the time-gated reflection matrix. In the present invention, the time-gated reflection matrix is applied to Singular value decomposition such that the time-gated eigenchannel corresponding to the depth of the target object is calculated, as one example. Herein, the Singular value decomposition can be described by [Formula 1]

$$R = U\Lambda V^{\dagger} \quad \text{[Formula 1]}$$

Herein, R represents the time-gated reflection matrix, V represents an unitary matrix whose columns contain eigenchannels at an input plane of the incidence beam, U represents an unitary matrix whose columns contain eigenchannels at an reflection plane of the reflection beam, and $\Lambda$ represents a diagonal matrix whose diagonal elements contain Singular values.

Each singular value and its squared value, or eigenvalue correspond to reflectance of the amplitude and intensity, respectively, for the associated the time-gated eigenchannel. Herein, the squared singular value which is plotted as blue dots in FIG. 3d is normalized by the reflectance of a random incident wave.

After the time-gated eigenchannel is calculated as mentioned above, a incidence beam having an incidence pattern to which the time-gated eigenchannel is applied (hereinafter, it is defined as 'eigen incidence beam') illuminates to the target object S14, and then the eigen incidence beam incident into the sample can be focused to the target object in the sample.

In the present invention, to form the eigen incidence beam by applying the time-gated eigenchannel to the incidence beam, the incidence wave which is identified from the columns of the matrix V in [Formula 1]. For example, j-th column of the matrix V is converted into a two-dimensional complex field image in the $\vec{r}_i$ input plane, which is the j-th eigenchannel with singular value of $\sigma_j$. In the present invention, the spatial light modulator which is applied to the setup in FIG. 1 controls the phase of the incidence wave, so that the eigenchannel can be applied to the incidence beam, as one example.

Figure 4A:
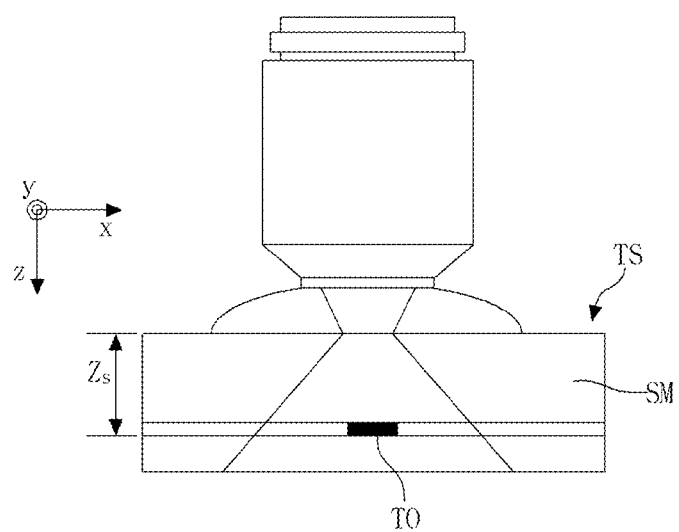
FIGS. 4a to 4g explain experimental examples of a method for focusing light to a target object within scattering medium according to the present invention.

Hereinafter, experimental results of the method for focusing the light to the target object within the scattering medium according to the present invention are explained. FIG. 4a is a test sample for testing the effect of the method for focusing the light to the target object within the scattering medium according to the present invention.

Figure 4B:
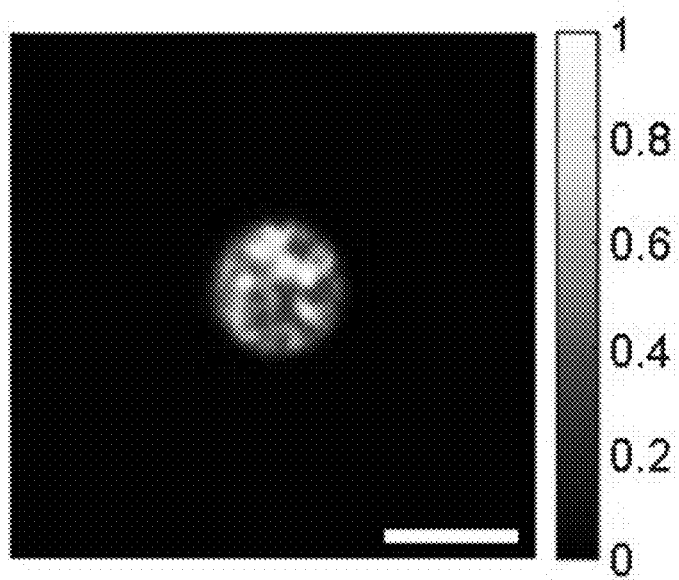

As shown in FIG. 4a, the target object wherein a silver disk with the diameter of 10 μm is coated on a 1 μm-thick transparent sheet of Poly methyl methacrylate (PMMA) is fabricated. FIG. 4b shows the reflection image of the target object exposed to free space.

The thickness of the silver disk was about 30 nm, which was thin enough that the transmittance measured right behind the disk was about 62.6%. Since the transmittance of the sliver disk is already known, the light intensity at the target object can be directly measured from the transmission measurement, as described about the setup in FIG. 1.

On the top of the target object, a scattering layer consisting of randomly dispersed 1 μm diameter polystyrene beads in Polydimethylsiloxane (PDMS) is placed. Scattering parameters of the scattering layer are $l_s$=48.5 μm and $l_t$=190 μm at a wavelength of 780 nm. The thickness of the scattering layer, that is the depth of the target object $z_s$ is varied from 1.9 $l_s$ to 6.8 $l_s$. Another scattering layer with similar scattering parameters of the scattering layer is placed at the bottom of the target object so that the silver disk is placed in the middle of the scattering medium. In the present invention, the silver disk which is the target object is embedded at $z_s$=331.7 μm (6.84 $l_s$ and 1.75 $l_t$), that is the distance from the surface of the scattering medium to the target object.

Figure 4C:
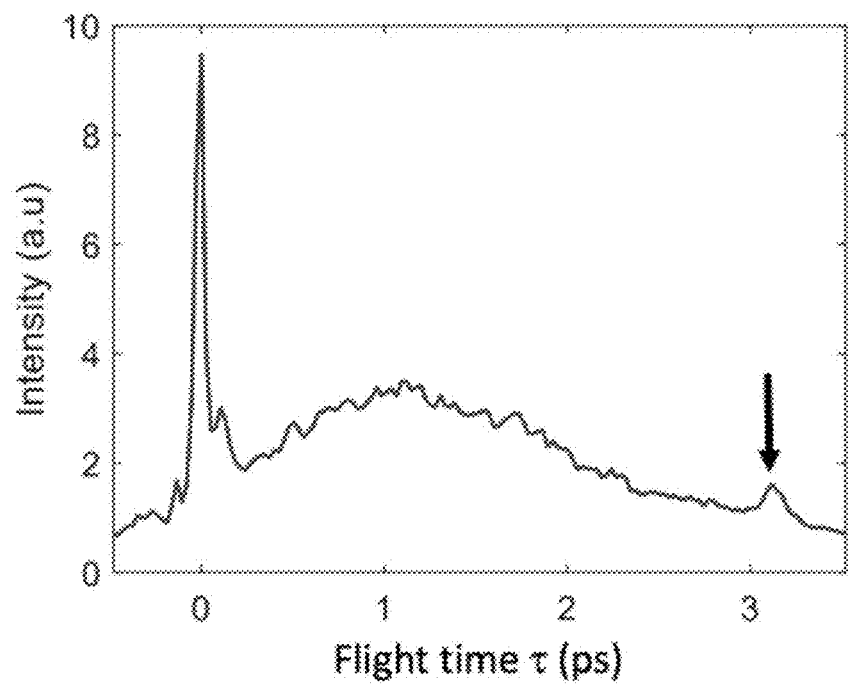

Time-gating reflection measurement is performed by using low-coherence interferometry. A random phase pattern is written on the wavefront of the output beam from a Ti:Sa laser (center wavelength: 780 nm, pulse width: 52 fs) illuminating the sample, and the total intensity of backscattered waves is measured as a function of the flight time, as shown in FIG. 4c.

A strong peak appears at the depth corresponding to the surface of the scattering medium due to the refractive index mismatch between materials of the objective lens and the scattering medium. In the present invention, the reflection from the scattering medium is set as a reference point, and the flight time at the reference point is set as '0'.

The width of the peak at the reference point is measured to be 7.8 μm, which is equal to the time-gating width of the imaging system according to the present invention determined by the pulse width of the light source. A small peak indicated by a black arrow appears at $\tau_0$=3.1 ps, which corresponds to the backscattered waves originating from the silver disk.

Figure 4D:
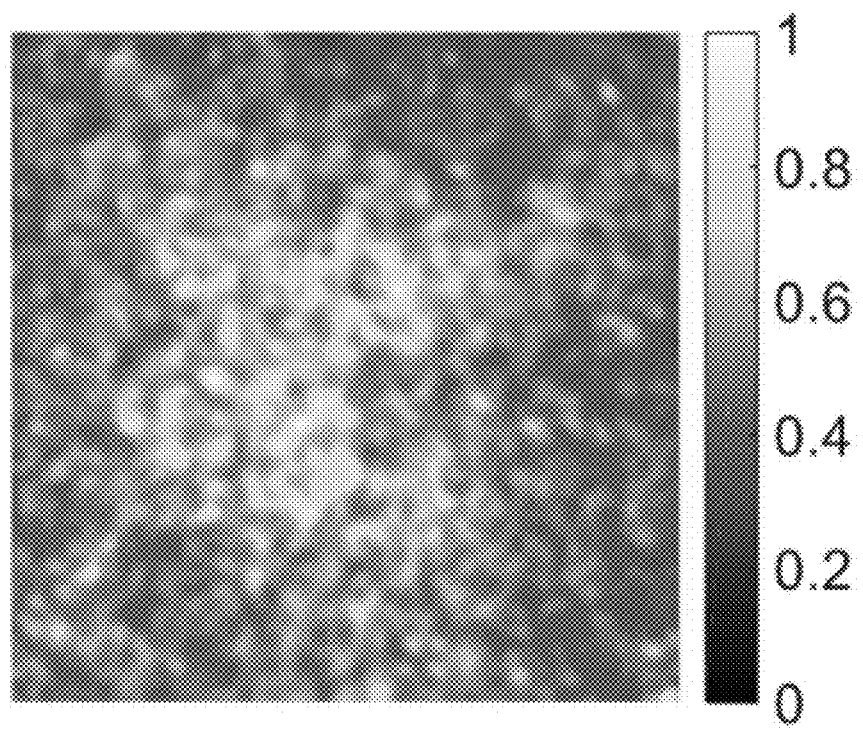

There are plenty of backscattering signals arriving at the other flight times, and the accumulated backscattering signal is 86 times larger than the signal at $\tau_0$. For this reason, the target object is completely invisible in the steady-state reflectance imaging in which backscattering from all time of flight are added together. The target object is invisible even in the angular compounding imaging time-gated at $\tau_0$ as shown in FIG. 4d as the backscattered waves get spread on its way back to a detector.

For the test sample in FIG. 4a, the time-gated reflection matrix is measured, as mentioned above, and the time-gated eigenchannel is calculated using the time-gated reflection matrix and then the experiment for illuminating the eigen reflection beam to the test sample is performed.

Figure 4E:
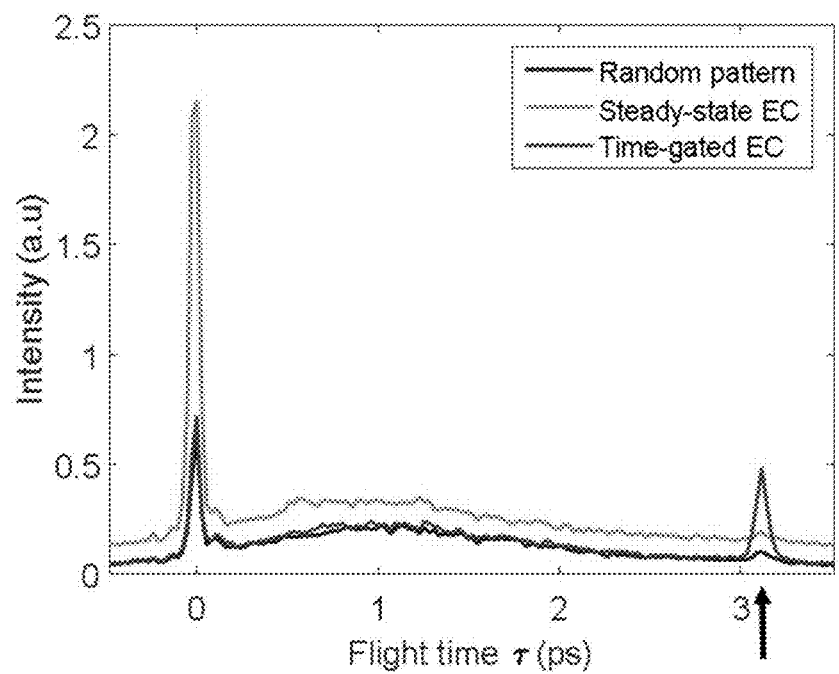

FIG. 4e is a graph which shows temporal response of the backscattered waves, a blue line is the temporal response for the random pattern input in FIG. 4c, and a red line is the temporal response for the input to which the time-gated eigenchannel is applied, that is for the eigen incidence beam. Also, a green line is the temporal response for a steady-state eigenchannel. As shown in FIG. 4e, the intensities at the other flight time are almost the same, but the intensity at the target flight time $\tau_0$=3.1 ps is increased by a factor of 3.8 in comparison with the random pattern input, and this suggests that the eigen incidence beam can be focused to the target object.

Figure 4F:
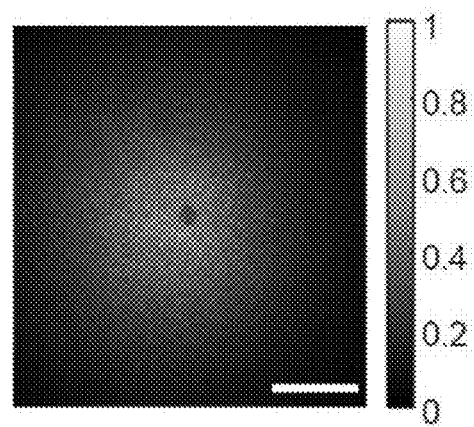
Figure 4G:
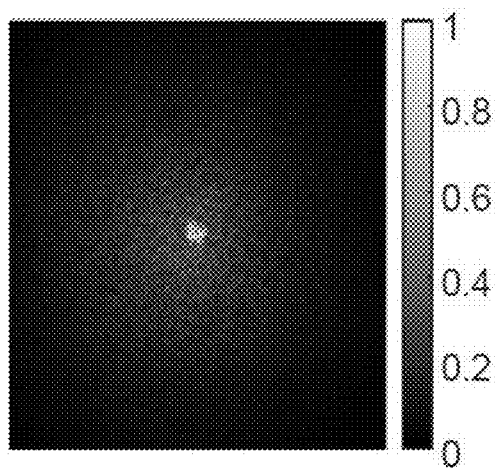

Also, the intensity of the light transmitted through the target object is measured by using the camera C2 in FIG. 1, and it is verified that when the eigenchannel is applied, the eigen incidence beam can be focused to the target object, as shown in FIGS. 4f and 4g. FIG. 4f is the transmission image for the random pattern input, and FIG. 4g is the transmission image for the eigen incidence beam according to the present invention.

Figure 5A:
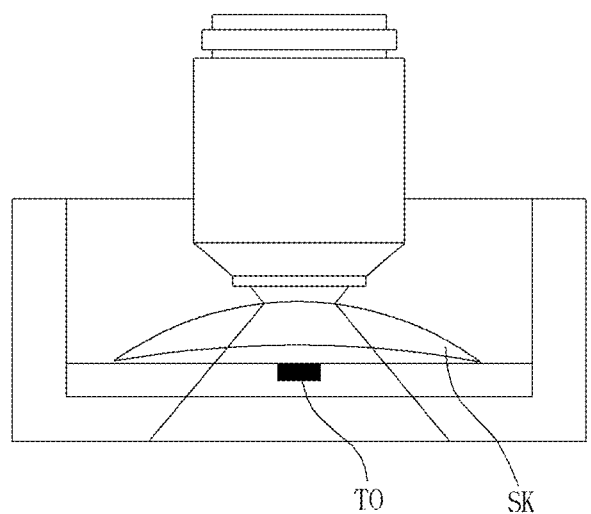
FIGS. 5a to 5f explain another experimental example of a method for focusing light to a target object within scattering medium according to the present invention.

Meanwhile, in the present invention, the experiment for verifying whether the light is focused to the target object located below a biological tissue is performed. As shown in FIG. 5a, the target object is placed under a skull SK from a three-day-old Sprague Dawley rat and the experiment is performed. The thickness of the skull is approximately 340 μm.

Figure 5B:
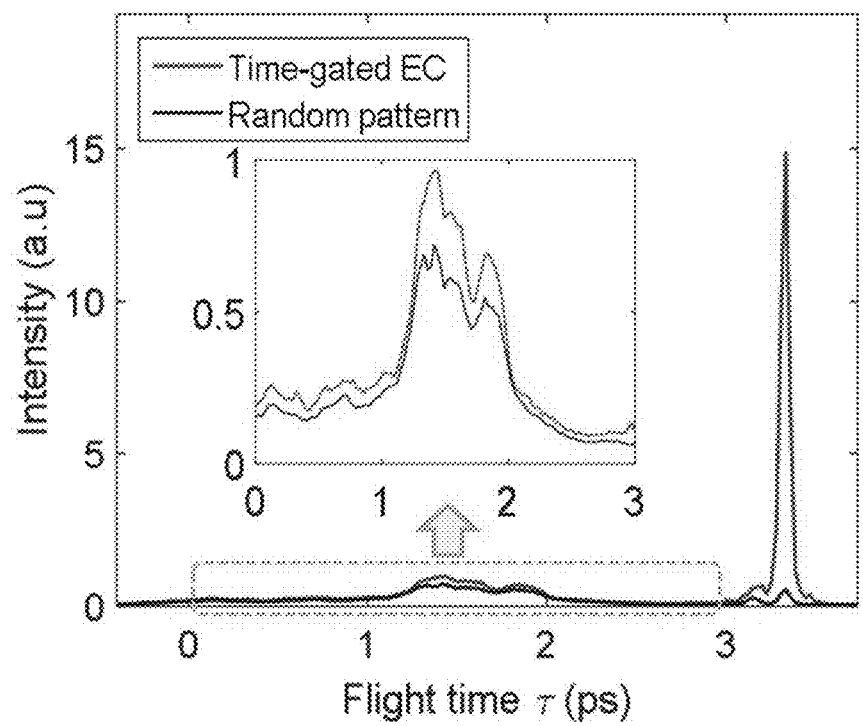

Two types of the target are prepared in this experiment. One is a 10 μm-diameter silver disk (hereinafter, it is defined as 'first target') which is the same with properties of the target object in FIG. 4a. the other is ten sparsely spread 3 μm-diameter silver disks (hereinafter, it is defined as 'second target') all with 30 nm thickness. The skull shows more complex temporal response of the backscattered waves than the artificial scattering samples due to its structural inhomogeneity, as shown in FIG. 5b. The intensity of backscattered waves is increased by a factor of 33.6 at the target flight time $\tau_0$=3.2 ps in comparison with the random input.

Figure 5C:
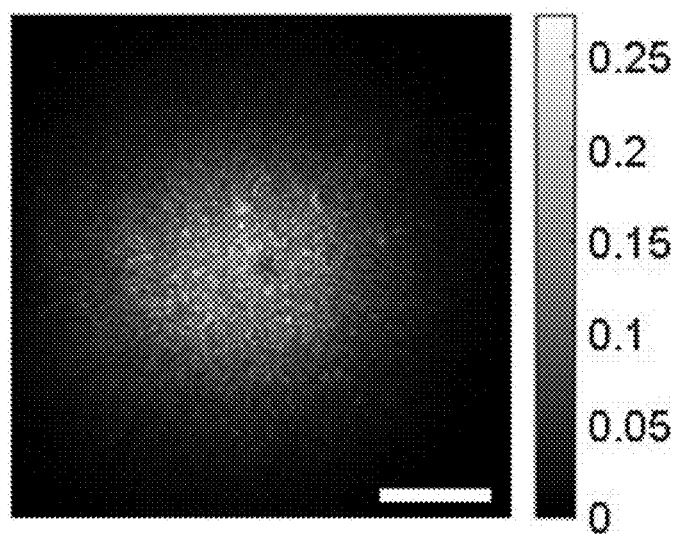
Figure 5D:
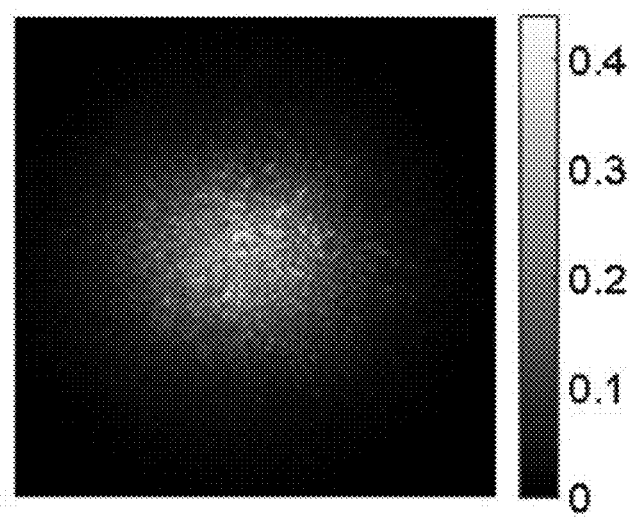
Figure 5E:
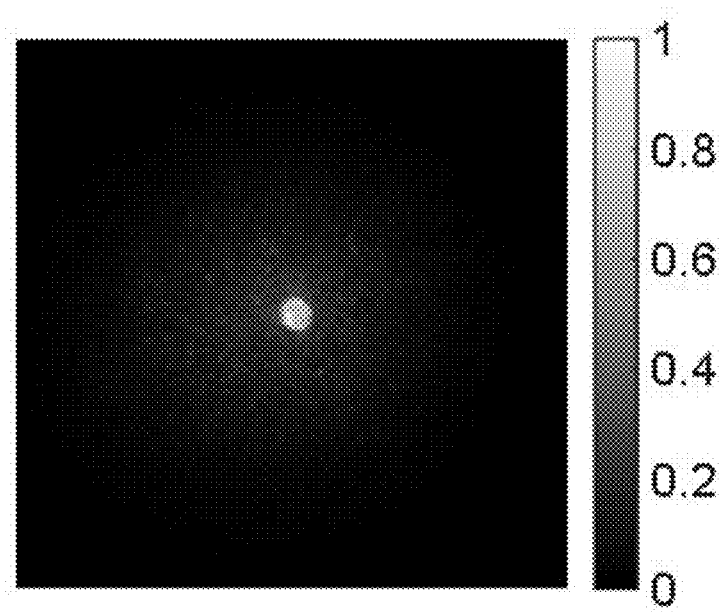
Figure 5F:
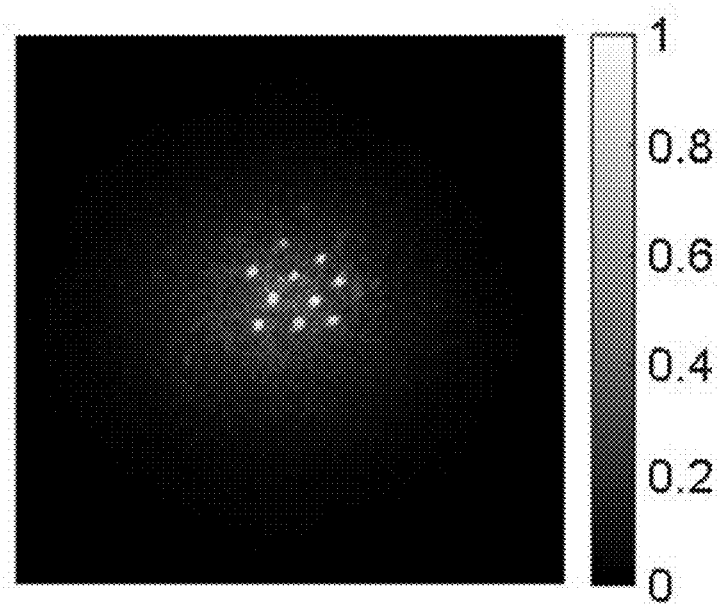

FIG. 5c is a recorded image of a transmitted wave when the random input illuminates to the first target, and FIG. 5d is a recorded image of a transmitted wave when the random input illuminates to the second target. Also, 5e is a recorded image of a transmitted wave when the eigen incidence beam to which the time-gated eigenchannel is applied illuminates to the first target, and FIG. 5d is a recorded image of a transmitted wave when the eigen incidence beam to which the time-gated eigenchannel is applied illuminates to the second target.

The maximum energy delivery enhancement to the target object was 12.4 in comparison with the random input for the first target. This result shows the potential of the present invention to efficiently focus energy through a skull, which is the main barrier for optical imaging and stimulation of nervous systems.

Although the embodiments of the present invention have been disclosed for illustrative purposes, those skilled in the art will appreciate that various modifications, additions and substitutions are possible, without departing from the scope and spirit of the invention as disclosed in the accompanying claims. It is thus well known to those skilled in that the patent right of the present invention should be defined by the scope and spirit of the invention as disclosed in the accompanying claims. Accordingly, it should be understood that the present invention includes various modifications, additions and substitutions without departing from the scope and spirit of the invention as disclosed in the accompanying claims.

The invention claimed is:

1. A method for focusing light to a target object within scattering medium comprising the following steps:
   (a) illuminating a plurality of incidence beams having different incidence patterns from each other, and obtaining reflection beams which are reflected from the target object for each incidence beams by a flight time which is a arrival time of the reflection beam to a camera;
   (b) forming a time-gated reflection matrix using the plurality of the incidence beams and the plurality of the reflection beams;
   (c) applying the time-gated reflection matrix to Single Value Decomposition such that a time-gated eigenchannel corresponding to a depth of the target object is calculated;
   (d) illuminating an eigen incidence beam having an incidence pattern, to which the time-gated eigenchannel is applied, to the target object.

2. The method for focusing light to the target object within scattering medium of claim 1, wherein the Single Value Decomposition in step (c) is processed by formula $$R=U\Lambda V^\dagger$$

wherein R is the time-gated reflection matrix, V is an unitary matrix whose columns contain eigenchannels at a incidence plane of the incidence beam, U is an unitary matrix whose columns contain eigenchannels at a reflection plane of the reflection beam, and $\Lambda$ is a diagonal matrix having singular values as diagonal elements; and
   wherein the time-gated eigenchannel is calculated by using eigenchannels at the columns of the matrix V.

3. The method for focusing light to the target object within scattering medium of claim 2, wherein the columns of the matrix V are converted to a two-dimensional complex amplitude image in the incidence plane such that the eigen incidence beam is formed in the step (d).

4. The method for focusing light to the target object within scattering medium of claim 2, wherein the time of the time-gated reflection matrix is calculated for a flight time of the incidence beam to the depth of the target object in scattering medium.

* * * * *